United States Patent
Matsui

(10) Patent No.: US 7,602,482 B2
(45) Date of Patent: Oct. 13, 2009

(54) OPTICAL INSPECTION METHOD AND OPTICAL INSPECTION APPARATUS

(75) Inventor: Shigeru Matsui, Hitachinaka (JP)

(73) Assignee: Hitachi High-Technologies Corporation, Tokyo (JP)

(*) Notice: Subject to any disclaimer, the term of this patent is extended or adjusted under 35 U.S.C. 154(b) by 308 days.

(21) Appl. No.: 11/798,805

(22) Filed: May 17, 2007

(65) Prior Publication Data

US 2007/0268484 A1 Nov. 22, 2007

(30) Foreign Application Priority Data

May 17, 2006 (JP) .............................. 2006-137212

(51) Int. Cl.
*G01N 21/00* (2006.01)
(52) U.S. Cl. ................. 356/237.3; 356/237.5
(58) Field of Classification Search ... 356/237.1–237.5; 250/559.42, 559.46
See application file for complete search history.

(56) References Cited

U.S. PATENT DOCUMENTS 5,798,829 A * 8/1998 Vaez-Iravani ............ 356/237.1

| | | | |
|---|---|---|---|
| 7,456,948 B2 * | 11/2008 | Togashi et al. ............ 356/237.2 |
| 2007/0268484 A1 * | 11/2007 | Matsui .................... 356/237.3 |
| 2008/0013076 A1 * | 1/2008 | Matsui ........................ 356/73 |
| 2008/0013084 A1 * | 1/2008 | Matsui et al. ............. 356/237.5 |
| 2009/0066941 A1 * | 3/2009 | Togashi et al. ............ 356/237.3 |

OTHER PUBLICATIONS

"Technical Handbook of Laser Process," pp. 226-230, Japan, with English translation (1992).

* cited by examiner

*Primary Examiner*—Hoa Q Pham
(74) *Attorney, Agent, or Firm*—McDermott Will & Emery LLP

(57) ABSTRACT

An optical inspection apparatus irradiates a light beam onto the outer surface of an object to be inspected, in the form of an illumination spot having an illumination intensity which is higher in the outer peripheral part of the object to be inspected than in the inner peripheral part thereof while uniformly maintains a temperature rise caused by the irradiation of the light beam, over the outer surface of the object to be inspected, in order to prevent the effective entire signal value of a scattered light signal from lowering, without lowering the linear speed of a movable stage for the object to be inspected in the outer peripheral part of the object to be inspected, thereby it is possible to prevent lowering of the detectability for a foreign matter or a defect, for preventing lowering of inspection throughput.

25 Claims, 4 Drawing Sheets

SIDE VIEW

PLAN VIEW

OPTICAL SYSTEM

OPTICAL INSPECTION METHOD AND OPTICAL INSPECTION APPARATUS

INCORPORATION BY REFERENCE

The present application claims priority from Japanese application JP2006-137212 filed on May 17, 2006, the content of which is hereby incorporated by reference into this application.

BACKGROUND OF THE INVENTION

1. Field of the Invention

The present invention relates to an optical inspection method and an optical inspection apparatus, irradiating a light beam onto an object to be inspected, such as a thin film substrate, a semiconductor substrate or a photomask, for detecting a foreign matter or a defect on the object to be inspected, and in particular an optical inspection method or an optical inspection apparatus, which enhance the detectability for a micro foreign matter or a micro defect.

2. Related Art

In a production line for a thin film substrates such as a semiconductor substrate, inspection for a foreign matter sticking to an outer surface of the thin film such as a semiconductor substrate has been carried out in order to monitor a condition of rising dust of a manufacturing apparatus. For example, it is required to detect a micro foreign matter or a micro defect, not greater than about 10 nm on the outer surface of a semiconductor substrate before formation of a circuit pattern thereon. Conventionally, in a technology for detecting a micro defect on the outer surface of an object to be inspected, such as a semiconductor substrate, as disclosed in U.S. Pat. No. 5,798,829, a focused laser beam is statically irradiated on to the outer surface of the semiconductor substrate (an area which is defined by the laser beam irradiated at this time onto the outer surface of the semiconductor substrate will be hereinbelow referred to as "illumination spot"), and scattered light from a foreign matter which possibly sticks to the semiconductor substrate that is fed on rotation or translation is detected so as to detect a foreign matter or a defect over the entire surface of the semiconductor substrate. An ellipsoidal mirror is used for detecting the scattered light, which is arranged in such a way that the primary focal position of the ellipsoid thereof is set at a detecting position on the semiconductor substrate while the secondary focal position thereof is set at an light receiving surface of a light receiving element, and the scattered light from a foreign matter is collected over a wide solid angle in order to detect even a micro foreign matter.

In the inspection apparatus for a foreign matter and a defect, as stated above, a movable stage for carrying an object to be inspected, capable of both rotation for main scanning and translation for sub-scanning in combination is usually used in order to, in general, spirally scan the object to be inspected. In a method for controlling the drive of the stage as mentioned above, there may be mainly carried out either constant linear velocity scanning with which an object to be inspected is scanned at a substantially constant linear velocity over its substantially entire surface, or a substantially constant angular velocity scanning with which the object to be inspected is scanned at a substantially constant angular velocity over its substantially entire surface. Above all, there may be often used the latter scanning, that is, the constant angular velocity scanning, in the case of the inspection is important.

If the inspection apparatus for a foreign matter and a defect according to the above-mentioned conventional technology, is used in the case of the constant angular velocity scanning, the substantially entire surface of the object to be inspected can be inspected at a speed nearly equal to the maximum speed of the movable stage for an object to be inspected. Accordingly, the inspection time can be shortened. Meanwhile, there has been caused such a problem that the detectability is different between the inner peripheral part and the outer peripheral part of the object to be inspected, and in particular, the detectability is lowered at the outer peripheral part of the object to be inspected. This is because the linear velocity is higher in the outer peripheral part than in the inner peripheral part in the constant angular velocity scanning so that the time for which a foreign matter or a defect passing through an illumination spot produces scattered light, diffracted light or reflected light becomes shorter than in the outer peripheral part. It has been known that scattered light, diffracted light or reflected light generated from a foreign matter or a defect is theoretically proportional to the intensity of illumination light, that is, the illumination intensity of an illumination spot. Since the "net signal value" of a detection signal of scattered light, diffracted light or reflected light is determined in general "(Intensity of Light to be detected)×(Duration Time of Produced Light)", the "net signal value" is less in the outer peripheral part so as to lower the detectability in such a condition that the illumination intensity is constant in the illumination spot.

This problem can be solved by lowering the linear velocity in the outer peripheral part. However, it causes lowering of the inspection throughput. There could be considered such a solution that the intensity of the illumination spot itself is sufficiently increased in order to enhance the detectability even in the outer peripheral part (the detectability in the inner peripheral part becomes, of course, extremely higher in this case). However, should the intensity of the illumination spot be higher, the energy generated by a laser beam to be irradiated would be excessively large, and accordingly, the temperature of the object to be inspected, in particular, the temperature in the vicinity of the outer surface thereof would be greatly increased, resulting in such a risk that the material or the structure of the object to be inspected would be damaged. Thus, increasing of the intensity of the illumination spot should be limited, and accordingly, the illumination intensity cannot be increased exceeding the limitation.

BRIEF SUMMARY OF THE INVENTION

Thus, the present invention is devised in view of the above-mentioned problems, and accordingly, an object of the present invention is to provide such a technology that the detectability for a foreign matter or a defect in the outer peripheral part of an object to be inspected can be restrained from lowering while thermal damage to the object to be inspected is prevented even in such a case that the inspection throughput is important, thereby it is possible to ensure satisfactory detectability over a substantially entire surface of the object to be inspected.

To the end, according to the present invention, there is provided the following configuration:

An optical inspection apparatus comprising a movable stage for moving an object to be inspected in a predetermined pattern, an illumination means for irradiating a light beam onto the surface of the object to be inspected, from a light source, and a light detecting means for detecting light which has been produced as a result of the irradiation of the light beam onto the surface of the object to be inspected, wherein the illumination means comprises an adjusting means for adjusting the brightness of the light beam irradiated onto the object to be inspected, in accordance with a moving speed of the movable stage for the object to be inspected.

The movable stage for an object to be inspected may be typically of a type such that the object to be inspected is on rotation while it is moved by a predetermined distance in a radial direction of the rotation (the rotation for a main scanning and the radial movement for an auxiliary scanning), or of a type such that the object to be inspected is rectilinearly reciprocated while it is moved by a predetermined distance in a direction substantially orthogonal to the reciprocating direction (translation for a main scanning and translation in the direction substantially orthogonal to the direction of the former translation). If the speed of this scanning is not uniform, it is desirable that the brightness of a light beam irradiated onto the object to be inspected is changed in accordance with the speed of the scanning in order to make the value obtained by multiplying the brightness of the irradiated light beam with a scanning time (brightness×scanning time) uniform, and accordingly, the detectability is constant at any position on the object to be inspected or the temperature rise of the object to be inspected heated by the irradiation of the light beam is constant. In particular, in the case of such a type that rotation with a constant angular velocity is used for the main scanning, since the liner scanning speed is higher on the outer peripheral side than on the inner peripheral side, the value of (brightness×scanning time) will be smaller on the outer peripheral side than on the inner peripheral side. In order to solve this problem, it is preferable to change the quantity of a light beam emitted from the light source or the intensity of the illumination spot in accordance with the linear speed.

According to the present invention, even in the outer peripheral part of the object to be inspected, where the linear speed should not be lowered since the throughput of the inspection is important, lowering of an effective entire signal value of a scatted light signal can be compensated by setting the intensity of the illumination spot to be greater than that of the inner peripheral part thereof, and accordingly, the detectability for a foreign matter or a defect can be restrained from lowering while thermal damage to the object to be inspected is prevented, thereby it is possible to ensure satisfactory detectability over the entire surface of the object to be inspected.

Explanation will be hereinbelow made of a preferred embodiment which comprises a movable stage for an object to be inspected, capable of rotational movement for main scanning, and of translational movement for auxiliary scanning, and adapted to carry out substantially continuous displacement in both main scanning direction and auxiliary scanning direction; a laser light source; an illumination means for irradiating a laser beam onto an outer surface of an object to be inspected in the form of an illumination spot having a predetermined size, a scattered, diffracted and reflected beam detecting means for detecting light scattered, diffracted and reflected in the illumination spot the object to be inspected, and converting thus detected light into electric signals; an A/D converting means for converting the electric signals into digital data; an inspection coordinate detecting means for detecting a position on the outer surface of the object to be inspected as inspection coordinate data at a time corresponding to the converted digital data during inspection; a determining means for a foreign matter or a defect, for determining the presence of a foreign mater or a detect which would be present on or around the outer surface of the object to be inspected in view of the electrical signal or the digital data; a particle size calculating means for calculating a size of the thus determined foreign matter or defect from the digital data; and a coordinate calculating means for a foreign matter or a defect, for calculating a position coordinate value of the foreign matter or the defect on the outer surface of the object to be inspected, from an information delivered from the inspection coordinate detecting means, wherein the rotational speed (angular speed) of the movable stage for an object to be inspected is maintained at a substantially constant value on the substantially entire surface of the object to be inspected.

In order to achieve the above-mentioned task, according to the present invention, the following measures are taken:

(1) controlling the light quantity of the laser light source so as to differ the intensity of the illumination spot between the inner peripheral part and the outer peripheral part of the object to be inspected, or alternatively (2) providing a light quantity adjusting means for adjusting the light quantity of a leaser beam emitted from the laser source; and, (3) controlling the light quantity adjusting means so as to change the intensity of the illumination spot from the outer peripheral part to the inner peripheral part of the object to be inspected or from the inner peripheral part to the outer peripheral part of the object and in particular, to cause the intensity of the illumination spot during inspection in the outer peripheral part to be higher than that in the inner peripheral part. This is because the illumination intensity of the light scattered, diffracted and reflected from the foreign matter or the defect is proportional to the intensity of the illumination spot, as stated above, and accordingly, a decrease in the "duration time of produced light" is compensated in the "net signal value" by increasing the intensity of the illumination spot. Meanwhile, the effect of increasing the temperature of the object to be inspected by a thermal energy from the irradiated laser beam, and in particular, the temperature around the outer surface thereof, is such that the temperature rise of the object to be inspected will be smaller as the linear speed of the object to be inspected is increased in the case of irradiating a laser beam onto the object to be inspected, which is moved without resting, if the illumination intensity of the irradiated laser beam is set to be constant, as explained in the following document 1. This is because, if the temperature with a tolerable temperature rise is contrarily set to be constant, it would result, the higher the linear moving speed, the higher the allowable illumination intensity of the laser.

Document 1: Technical Handbook of Laser Process, pages 226 to 230

Thus, according to the present invention, the above-mentioned control includes the following techniques:

(4) controlling being based upon a linear speed which is determined in combination of a rotational speed (for main scanning) and a translational speed (for auxiliary scanning) of the movable stage for an object to be inspected;

(5) controlling on the basis of auxiliary scanning coordinate information as to the movable stage for an object to be inspected;

(6) incorporating a light quantity control table in which information as to relationships between auxiliary scanning coordinates of the movable stage for an object to be inspected, and as to the intensity of the illumination spot at the coordinates position has been beforehand stored; and (7) controlling in accordance with auxiliary scanning coordinate information of the movable stage for an object to be inspected, and the light control table. Further, according to the present invention, the change of the intensity of the illumination spot is controlled so that:

(8) a temperature rise caused at the outer surface of the object to be inspected by irradiation of a laser beam is maintained substantially constant over the outer surface of the object to be inspected in a part or in its entirety; or (9) the intensity of the illumination spot will be proportional to a substantially ½-th power of the linear speed at the outer surface of the object to be inspected in part or in its entirety.

Further, according to the present invention, since the intensity of the illumination spot is changed, it is required to compensate an influence which is present in the intensity of the scatted light, caused by the change of the intensity, and accordingly, the present invention includes:

(10) causing the above-mentioned determining means for a foreign object or a defect and the particle size calculating means to correct the above-mentioned digital data with the intensity of the illumination spot at the time corresponding to the digital data, and further includes, for this correction;

(11) incorporating an illumination light quantity adjusting means for monitoring a light quantity proportional to the intensity of the illumination spot in the optical path from the laser light source or the light quantity adjusting means to the illumination spot.

The present invention will be explained hereinbelow in detail in the form of preferred embodiment of the present invention with reference to the accompanying drawings in which:

DETAILED DESCRIPTION OF THE INVENTION

Figure 1:
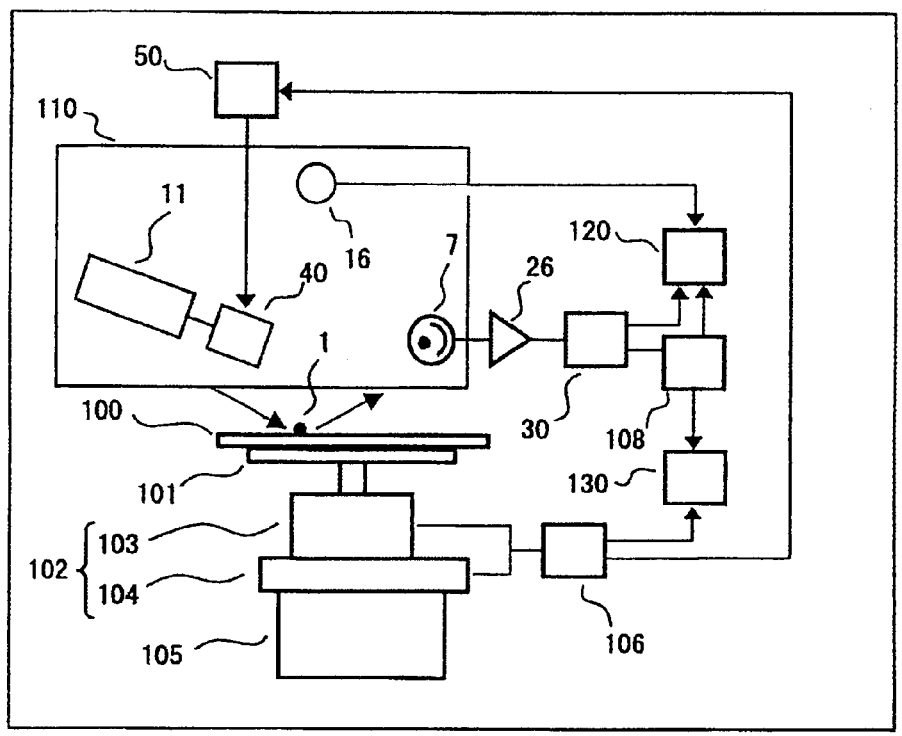
FIG. 1 is a view for illustrating a first embodiment of an inspection apparatus for a foreign matter or a defect, according to the present invention.
Figure 2:
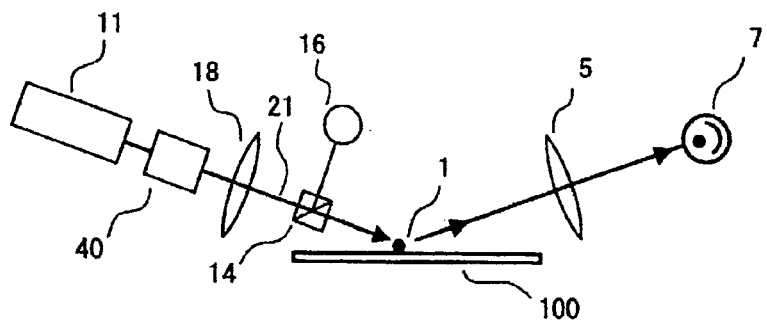
FIG. 2 is a view illustrating an configuration of an optical system in the first embodiment of the present invention.
Figure 2:
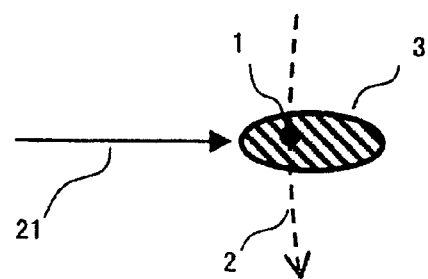

Referring to FIG. 1 which shows a first embodiment of an inspection apparatus for a foreign matter and a defect, utilizing a method of detecting a foreign matter or a defect, according to the present invention. A semiconductor wafer 100 as an object to be inspected is sucked under vacuum to a vacuum chuck 101 which is mounted on a movable stage 102 for an object to be inspected, composed of a rotation stage 103 and a translation stage 104 and on a Z-stage 105. Illumination/detection optics 110 which are arranged above the semiconductor wafer 100 is shown in FIG. 2. That is, a laser light source is used as a illumination light source 11. A laser beam from the light source 11 is incident upon a light quantity adjusting mechanism 40 so as to be attenuated in order to have a required light intensity, and thereafter is incident, in the form of an irradiation beam 21 upon an irradiation lens 18 so as to form an illumination spot 3 having a predetermined size. In this embodiment, as the above-mentioned light quantity adjusting mechanism 40, a light attenuator is composed of a polarizer or a polarized beam splitter, and a half wave plate in combination. However there may be used another one such as a filter whose light transmittance changes, or the one in which the light quantity is adjusted by changing the temporal modulation with the use of an acoustooptic modulator, utilizing the other principles. The illumination light beam has, for example, P-polarization, and is adapted to be incident upon the outer surface of the semiconductor wafer 100, obliquely thereto with a Brewster angle with respect to crystal Si. Thus, the illumination spot 3 has a substantially elliptic shape. It is noted that the inside of the contour at which the intensity of the illumination spot is decreased to a value of one in square of e of the center part of the illumination spot ($1/e^2$ where e is the base of natural logarithm) is, at this stage, defined as the illumination spot 3. The widths of the illumination spot 3 in the direction of the major axis and in the direction of the minor axis will be hereinbelow referred to d1 and d2, respectively. In the optical path for the illumination light beam 21, there are provided a beam splitter 14 for extracting a part of the illumination light beam 21 and a photodiode 16 for converting an intensity of the thus extracted part of the light beam into an electrical signal in order to monitor the quantity of the irradiated light beam. Further, a condenser lens 5 is designed so as to condense scattered light with a low elevation angle in order to catch the scattered light from a micro foreign object which obeys Rayleigh scattering. With this configuration, a foreign object 1 passes over the illumination spot 3, and accordingly, a scattered light signal can be obtained from a photo detector 7. In this embodiment, as the photo detector 7, although a photo multiplier tub is used, there may be used another photo detector capable of detecting scattered light from a foreign matter with a high degree of sensitivity, utilizing another principle. The scattered light signal from the photo detector 7 is amplified by an amplifier 26, thereafter, is sampled at every sampling interval ΔT which has been determined beforehand at an A/D converter 30, and is then converted into digital data. Which digital data is compared by a determination mechanism 108 for a foreign object and a defect, with a detection threshold. The determination mechanism 18 for a foreign matter and a defect determines, if the digital data is not less than the threshold, the digital data as the one which is caused by a foreign matter or a defect, and delivers determination information as to the presence of a foreign matter or a defect. It is noted that, instead of such a determination that digital data obtained from the A/D converter 30 is compared with the predetermined threshold so as to determine the presence of a foreign matter, an output electric signal from the amplifier 26 may be compared with a predetermined threshold voltage in order to determine whether a foreign matter or a defect is present or not. When the determination information as a foreign matter or a defect is delivered, a coordinate detecting mechanism 130 calculates a coordinate position of the detected foreign matter or defect. After the coordinate position of the foreign matter or defect is obtained, a particle size calculating mechanism 120 calculates a size of the detected foreign matter or defect from maximum digital data among measured values corresponding to the foreign matter or defect. It is noted that in the case of changing the intensity of the illumination spot 3 by the light quantity adjusting mechanism 40, the sized is calculated, after the maximum digital data is compensated with an illumination intensity monitored by the photodiode 16 since the intensity of scatted light becomes different even with the one and the same foreign matter, corresponding (in proportion) to the changing of the intensity.

Figure 3:
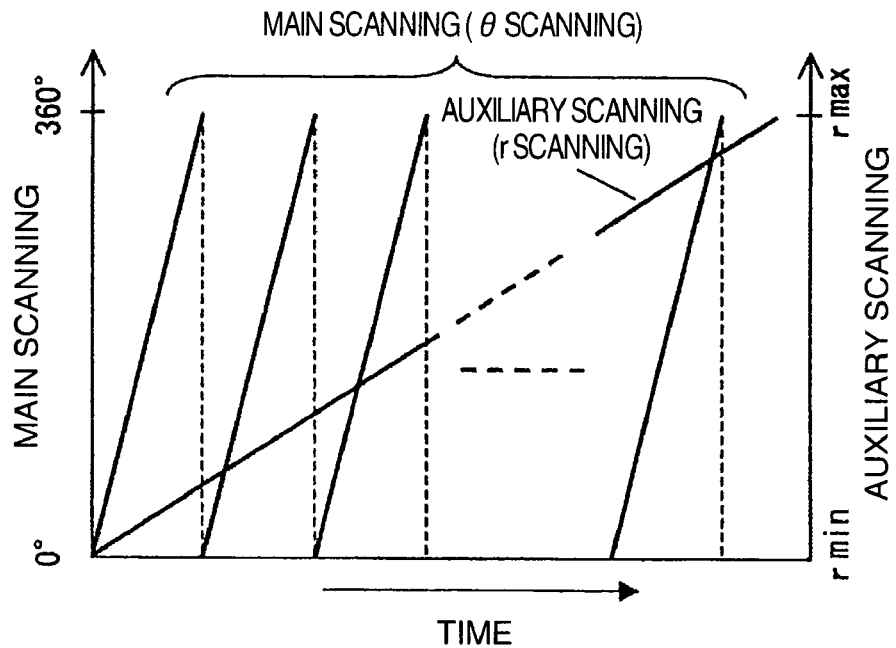
FIG. 3 is a view for explaining a driving method of driving a movable stage for an object to be inspected, for spirally scanning.
Figure 4:
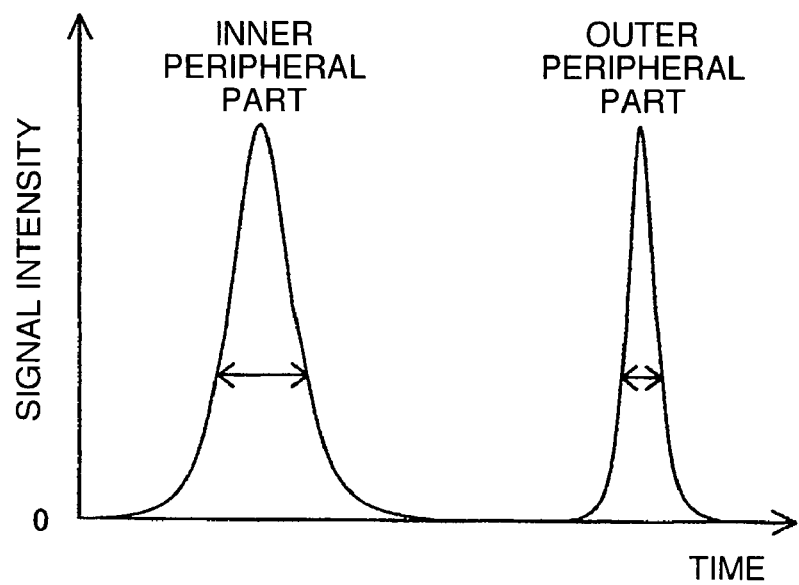
FIG. 4 is a view for explaining difference in signal waveform between the inner peripheral part and the outer peripheral part of an object to be inspected.

In this embodiment, the movable stage 102 for an object to be inspected spirally scan the outer surface of the semiconductor wafer 100, substantially in its entirety, with the illumination spot 3 in combination of rotational movement θ for the main scanning and translational movement r for the auxiliary scanning with the time as shown in FIG. 3. The major axis of the illumination spot 3 is taken along the direction of the auxiliary scanning of the movable stage for an object to be inspected. The movable stage 102 for an object to be inspected is mounted thereon with an inspection coordinate detecting mechanism 106 for detecting the main scanning coordinate position θ and the auxiliary scanning coordinate position r during inspection. In this embodiment, although there are used an optical read-out type rotary encoder for detecting the main scanning coordinate position θ and an optical read-out type linear encoder for detecting the auxiliary scanning coordinate position r, there may be used any sensor using other principles if it can accurately detect an angular position or a linear position. Each time when the rotary stage is rotated by one complete turn, the auxiliary scanning shifts by Δr. should Δr>d1, no illumination light beam would be irradiated onto the semiconductor wafer 100 during spiral scanning, and accordingly, a gap zone which cannot be inspected will occur. Thus, Δr<d1 is usually set. In this embodiment, the scanning for the semiconductor wafer 100 is carried out from the inner peripheral part to the outer peripheral part thereof. However, the scanning may be also made reversely. Further, in this embodiment, the rotary stage 103 is driven at a substantially constant angular speed while the translation stage 104 is driven at a substantially constant linear speed over a substantially entire zone from the inner peripheral part to the outer peripheral part of the semiconductor wafer. As a result, the relative linear speed of the illumination spot 3 with respect to the outer surface of the semiconductor wafer 100 is higher in the outer peripheral part that in the inner peripheral part. Thus, the time during which a foreign matter on the semiconductor wafer 100 passes across the distance d2 of the minor axis is shorter when the foreign matter is present in the outer peripheral part of the semiconductor wafer 100 than when the foreign matter is present in the inner peripheral part thereof. And accordingly, as shown in FIG. 4, a time-varying waveform of a scattered light signal which is obtained from the photo detector 7 by way of the amplifier 26 is, the larger the radius position, that is, the nearer to the outer peripheral part at which the foreign matter is present, in the direction of the auxiliary scanning, the smaller the half-value width of a signal peak. It may be considered that the effective entire signal value of a scattered light signal which is delivered when a foreign matter or a defect passes once over the illumination spot 3 is substantially in proportion to the area of the signal peak waveform. Meanwhile, noise components upon detection of a foreign matter or a defect are in general dominated by shot noise derived from background scatted light generated on the illumination spot 3 zone, and the light quantity of the background scatted light is constant, not depending upon the above-mentioned linear speed. Thus, if the size and the intensity of the illumination spot 3 are constant while the movable stage for an object to be inspected is driven at a constant main scanning rotational speed and at a constant auxiliary scanning linear speed, the effective entire signal value is smaller when the object is present in the outer peripheral part than when the one and the same object is present in the inner peripheral part. Thus, it may be easily anticipated that the S/N ratio in the signal direction would be decreased. It is, of course, possible to prevent the effective entire signal value from being lowered, by lowering the linear speed of the movable stage for a foreign matter or a defect in the outer peripheral part. In this case, it may be also easily anticipated that it incurs lowering of the inspection throughput.

Further, consideration is made about the difference between the inner and outer peripheral parts of the semiconductor wafer 100 in another view point, if the size and the intensity of the illumination spot 100 are constant, the near to the outer peripheral part, the position of a point on the semiconductor wafer 100, the higher the linear speed, the time during which the point passes across the distance d2 of the minor axis becomes shorter. On the contrary, as viewed from the point on the semiconductor wafer, since the illumination spot having one and the same size and one and the same illumination intensity passes thereover in a short time, it would be easily anticipated with a natural conclusion that the whole heat value given by the irradiation beam within a predetermined travel time would be less, and that as a result, a temperature rise caused around the point as stated above would be less. Indeed, the above-mentioned document 1 discloses that the temperature rise around a specific point is in reverse proportion to ½-th power of a moving speed of a heat source as a result of calculation in the case of movement of the heat source. On the contrary, considering such a task that the temperature rise at the outer surface of the semiconductor wafer 100 is maintained to be constant, it can be understood that the optical input or the illumination intensity can be larger as the position is located nearer to the outer peripheral part if the size of the illumination is constant in view of the following formula:

Temperature Rise∝Averaged Illumination Spot Intensity/(½th Power of Linear Moving Speed of Heat Source) ∴under such a condition that the temperature rise is constant, Averaged Illumination Spot Intensity/(½th Power of Linear Moving Speed of Heat Source)=Constant Meanwhile, since it has been well-known that the intensity of scattered light from a foreign matter or a defect is in proportion to an intensity of illumination to the foreign matter or the defect, such a fact that the illumination intensity can be larger as the linear speed is higher, enables compensation for such an unfavorable effect that the above-mentioned effective entire signal value becomes lower as the above-mentioned linear speed is higher, although it is not perfect. Thus, in this embodiment, the allowable value Pmax in the above-mentioned formula: [Averaged Illumination Spot Intensity/(½-th Power of Linear Moving Speed of Heat Source), has been previously obtained, depending upon characteristics of the semiconductor wafer 100. Further, during actual inspection, an illumination intensity control part 50 receives information as to a linear speed from the movable stage 102 for an object to be inspected, so as to control the light adjusting mechanism 40 in order to set the intensity of the illumination spot 3 to an allowable illumination intensity value which is determined from the Pmax and the above-mentioned information as to the linear speed. As a result, the intensity of the illumination spot 3 can be higher in the outer peripheral part than in the inner peripheral part, lowering of the sensitivity caused by a difference in the linear speed can be compensated although it is not perfect, thereby it is possible to improve the detectability for a foreign matter or a defect over the entire zone from the inner peripheral part to the outer peripheral part in comparison with a conventional inspection apparatus for a foreign matter or a defect. However, should the illumination spot 3 overlap around the outer peripheral edge part of the semiconductor wafer 100, that is, the wafer edge, extremely large scatted light would be produced in comparison with that of a usual foreign matter or defect, and the light detector 7 would saturate, resulting in impossible detection of a foreign matter or a defect. Thus, in this embodiment, although the illumination intensity control part 50 gradually increases the intensity of the illumination spot 3 toward the outer peripheral part of the semiconductor wafer 100, the illumination intensity control part 50 contrarily restrains the intensity of the illumination spot 30 when the latter comes to a position in the vicinity of the wafer edge.

Figure 5:
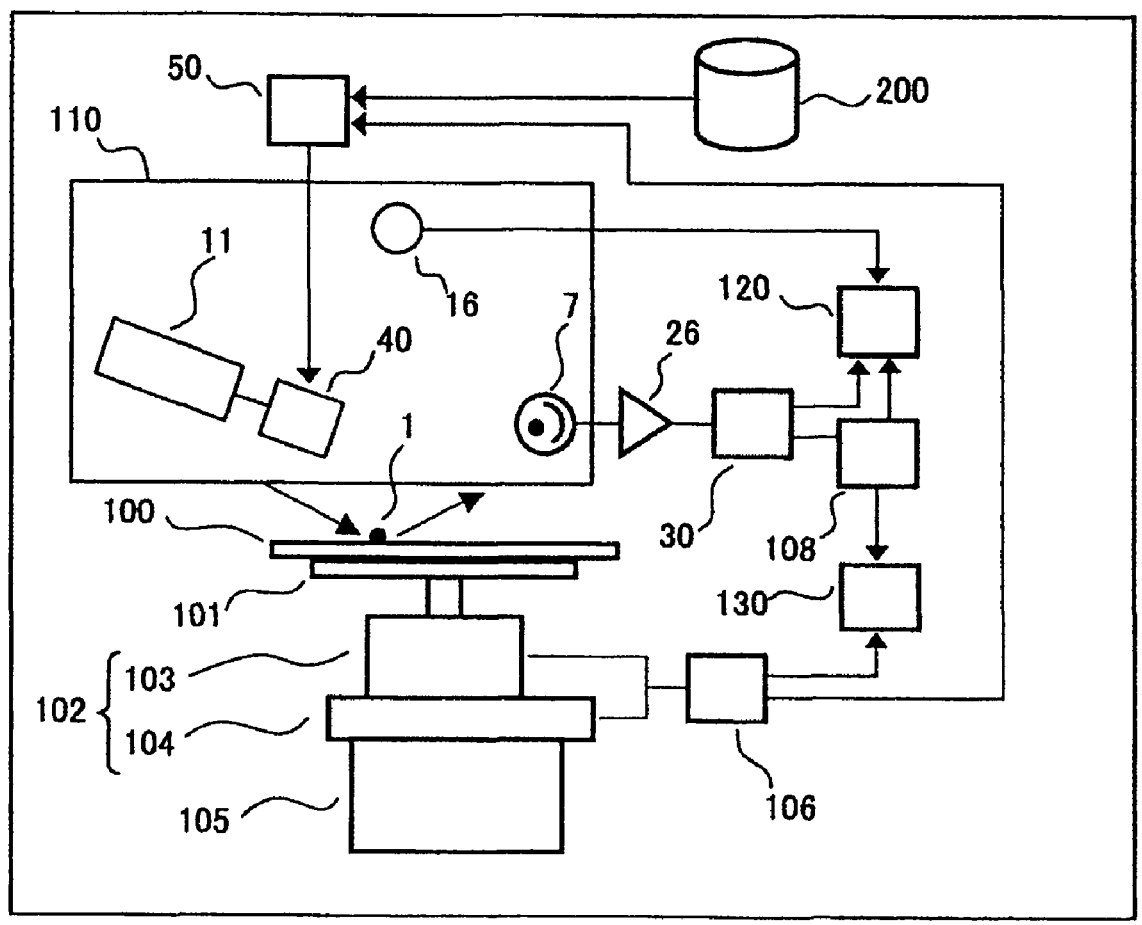
FIG. 5 is a view illustrating a second embodiment of a inspection apparatus for a foreign object and a defect, according to the present invention.
Figure 6:
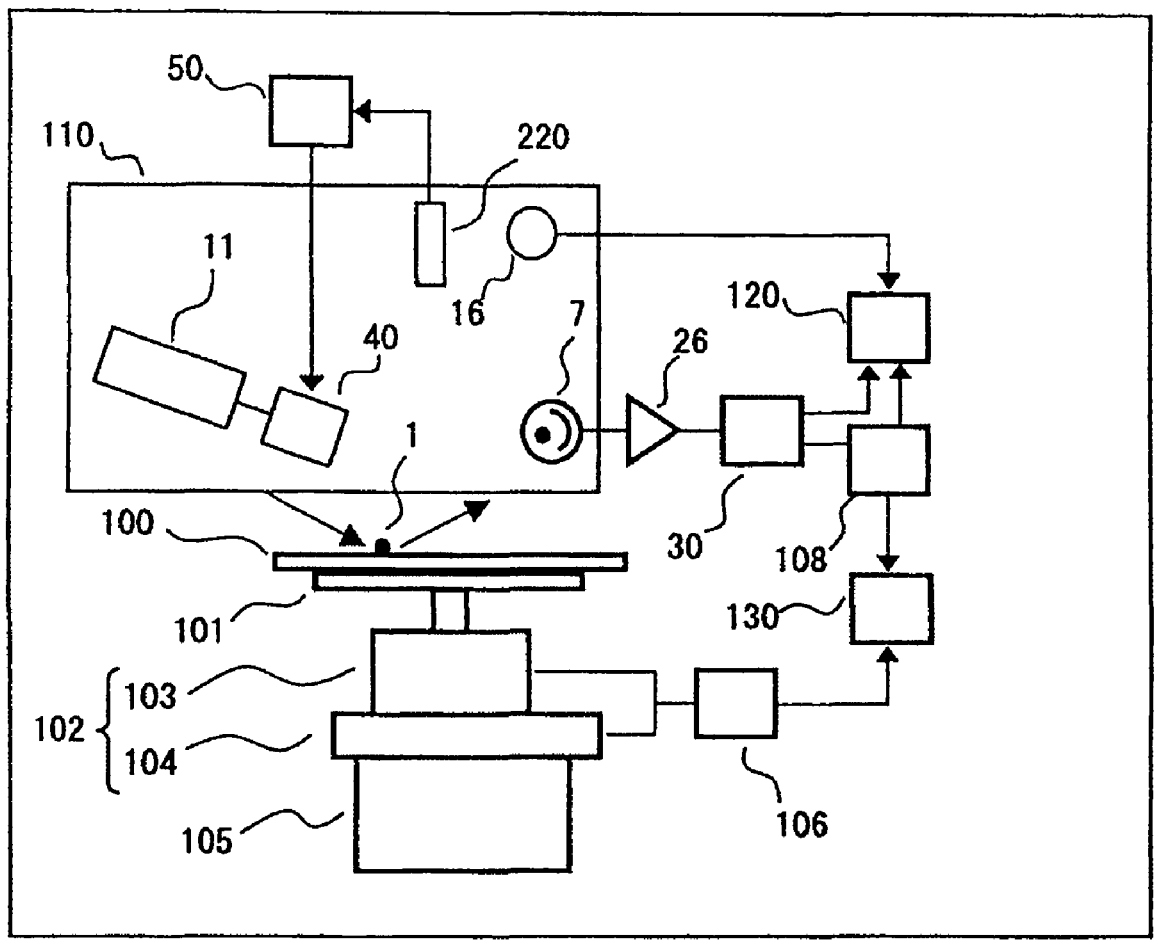
FIG. 6 is a view illustrating a third embodiment for a foreign object and a defect, according to the present invention.
Figure 6:
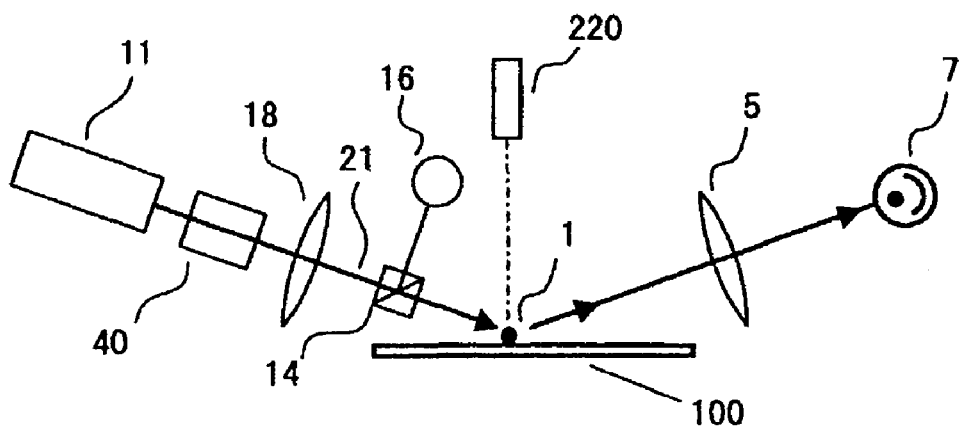

In the first embodiment, the illumination intensity is controlled on the basis of the information as to the linear speed from the movable stage 102 for an object to be inspected. However, in the case of driving at a constant main scanning rotational speed and at a constant auxiliary scanning speed, the control can be made on the basis of an auxiliary scanning coordinates (that is, a radius) from the inspection coordinate detecting mechanism 106, instead of the information as to the linear speed since the linear speed determined in combination of the main scanning and the auxiliary scanning is proportional to a radius as the auxiliary scanning coordinates. Although these are based upon such a fact that a temperature rise at a specific point is in inverse proportion to ½-th power of the moving speed of a heat source, as disclosed in the document 1, such a possibility of occurrence of an effect which does not satisfy this rule, could not be completely negated in view of a material of the semiconductor wafer 100. In order to control the illumination intensity even in such a case, illumination intensity should not be determined mathematically and unequivocally from the information as to the linear speed and the radius, the following measure may be taken: that is, a data base have been built up as to relationships among illumination intensities, linear speeds and temperature rises after confirmation under testing or the like while the inspection apparatus for an object to be inspected is incorporated therein with a light quantity control table 200 in which relational data between linear speeds and allowable illumination intensities have been stored, and during practical inspection, the illumination control part 50 receives information as to a linear speed from the movable stage 102 for a foreign matter or a defect, and reads an allowable illumination intensity value with which the intensity of the illumination spot 3 on the semiconductor wafer 100 corresponds to the above-mentioned information as to the linear speed, from the light quantity control table 200 in order to control the light quantity adjusting mechanism 40. This configuration is shown in FIG. 5, as a second embodiment. Further, with the use of a surface temperature sensor 220 capable of measuring a surface temperature in a micro area, a surface temperature of the illumination spot 3 part on the semiconductor wafer 100 may be directly measured during inspection so as to control the light quantity adjusting mechanism 40 in order to prevent the measured temperature value from exceeding the allowable value. This configuration is shown in FIG. 6 as a third embodiment.

It is noted in the configuration of the above-mentioned embodiment that the quantity of a laser beam emitted from the laser light source 11 is changed by the above-mentioned light quantity adjusting mechanism 40. However, if there is used a laser light source capable of directly changing its output power by changing its drive current or the like, the light source 11 itself may be, of course, directly controlled so as to change the light quantity therefrom with no provision of the light quantity adjusting mechanism. Further, in such a case that the semiconductor wafer 100 has, on the outer surface thereof, a circuit pattern, the illumination intensity may be controlled in view of characteristics of a material which is sensitive to thermal effects among materials which constitute the circuit pattern.

Thus, with the above-mentioned embodiments, even in the outer peripheral part of an object to be inspected, where lowering of the linear speed of the stage is undesirable in view of the inspection throughput, it is possible to compensate lowering of the effective entire signal value of a scattered light signal by allowing the intensity of the illumination spot to be larger in the outer peripheral part than in the inner peripheral part of an object to be inspected while the temperature rise of an object to be inspected is maintained to be constant.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An optical inspection method comprising the steps of:
providing a movable stage for an object to be inspected, capable of rotational movement for main scanning and translational movement for auxiliary scanning, and adapted to be substantially continuously displaced in both main scanning direction and auxiliary direction, a laser light source, an illumination means for irradiating a laser beam emitted from the laser light source, onto the outer surface of an object to be inspected in the form of an illumination spot having a predetermined size, a scattered/diffracted/reflected light detecting means for detecting light scattered, diffracted and reflected in the illumination spot of the irradiated beam, and converting the detected light into electric signals, an A/D converting means for converting the electric signals into digital data, an inspection coordinate detecting means for detecting a position on the outer surface of the object to be inspected at a time corresponding to the converted digital data, as inspection coordinate data, during inspection, an object/defect determination means for determining the presence of a foreign matter or a defect which is present on the outer surface of the object to be inspected or in the vicinity of the outer surface thereof, from the electric signal or the digital data, a particle size determining means for calculating the size of the thus determined foreign matter or defect, from the digital data, a foreign matter/defect coordinate calculating means for calculating a position coordinate value of the foreign matter or the defect on the outer surface of the object to be detected, from information delivered from the inspection coordinate detecting means; and detecting a foreign matter or a defect which is present on or in the vicinity of the outer surface of the object to be inspected by moving and scanning the object to be inspected at a linear speed which is different between the inner peripheral part and the outer peripheral part of the object to be inspected;

wherein said detecting step includes a step of controlling the light quantity of the laser light source so as to change the intensity of the light spot between the inner peripheral part and the outer peripheral part of the object to be inspected.

2. An optical inspection method as set forth in claim 1, wherein the intensity of the illumination spot is controlled on the basis of a linear speed which is determined in combination of a rotational speed (main scanning speed) and a translational speed (auxiliary scanning speed) of the movable stage for an object to be inspected.

3. An optical inspection method as set forth in claim 2, wherein the intensity of the illumination spot is controlled so as to a value which is in proportion to about ½-th power of the linear speed over the outer surface of the object to be inspected in part or in its entirety.

4. An optical method as set forth in claim 2, wherein the intensity of the illumination spot is controlled so that temperature rise at the outer surface of the object to be inspected caused by the irradiation of the laser beam thereonto is maintained to be constant over the outer surface of the object to be inspected in part or in its entirety.

5. An optical inspection method as set forth in claim 1, wherein the intensity of the illumination spot is controlled on the basis of an information of auxiliary scanning coordinates of the movable stage for an object to be inspected.

6. An optical inspection method as set forth in claim 5, further comprising steps of providing a light quantity control table for previously storing information as to a relationship between the auxiliary scanning coordinates of the movable stage for an object to be inspected and as to the intensity of the illumination spot at the coordinate position; and controlling the intensity of the illumination spot in accordance with the information of the auxiliary scanning coordinates of the movable stage for an object to be inspected, and the light quantity control table.

7. An optical inspection method as set forth in claim 6, wherein the information of the intensity of the illumination spot in the light quantity table is determined so that the temperature rise caused at the outer surface of the object to be inspected, by the irradiation of the laser beam thereonto is maintained to be substantially constant over the outer surface of the object to be inspected in part or in its entirety.

8. An optical inspection method as set forth in claim 1, further comprising the step of correcting the digital data with the intensity of the illumination spot at the time corresponding to the digital data by use of the foreign matter/defect determining means and the particle size calculating means.

9. An optical inspection method as set forth in claim 8, further comprising the steps of providing an illumination light quantity monitor for monitoring a light quantity in proportion to the intensity of the illumination spot on an optical path from the laser light source or the light quantity adjusting means to the illumination spot, correcting the digital data with the use of a signal from the light quantity monitor by use of the foreign object/defect determining means and the particle size calculating means.

10. An optical inspection method as set forth in claim 1, wherein the intensity of the illumination spot is restrained to a lower value on the outer peripheral edge of the object to be inspected.

11. An optical inspection method comprising the steps of providing a movable stage for an object to be inspected, capable of rotational movement for main scanning and translational movement for auxiliary scanning, and adapted to be continuously displaced in both main scanning direction and auxiliary scanning direction, a laser light source, a light quantity adjusting means for adjusting a light beam emitted from the laser light source, an illumination means for irradiating a light beam emitted from the light quantity adjusting means onto the outer surface of the object to be inspected in the form of an illumination spot having a predetermined size, a scattered/diffracted/reflected light detecting means for detecting light scattered, diffracted and reflected in the illumination spot of the irradiated light beam, and converting the detected light into electric signals, an A/D converting means for converting the electric signals into digital data, an inspection coordinate detecting means for detecting a position on the outer surface of the object to be inspected at a time corresponding to the converted digital data, as inspection coordinate data, during inspection, a foreign matter/defect determining means for determining the present of a foreign matter or a defect which is presence on or in the vicinity of the outer surface of the object to be inspected, from the electric signals or the digital data, a particle size detecting means for calculating a size of the determined foreign matter or defect from the digital data, a foreign matter/defect coordinate calculating means for calculating a position coordinate value of the foreign matter or defect on the outer surface of the object to be inspected, from information delivered from the inspection coordinate detecting means; and detecting a foreign matter or a defect which is present on or in the vicinity of the outer surface of the object to be inspected by moving and scanning the object to be inspected at a linear speed which is different between the inner peripheral part and the outer peripheral part of the object to be inspected; wherein said detecting step includes a step of controlling the light quantity adjusting means so as to change the intensity of the illumination spot from the inner peripheral part to the outer peripheral part of the object to be inspected, or the outer peripheral part to the inner peripheral part thereof.

12. An optical inspection apparatus comprising:
a movable stage for moving an object to be inspected in a predetermined pattern,
an illumination means for irradiating an illumination light beam from a light source onto the outer surface of the object to be inspected, and
a light detecting means for detecting light produced as a result of the irradiation of the illumination light beam onto the outer surface of the object to be inspected,
wherein the illumination means includes an adjusting means for adjusting the brightness of the light beam irradiated onto the outer surface of the object to be inspected, depending upon a moving speed of the movable stage for an object to be inspected.

13. An optical inspection apparatus as set forth in claim 12, wherein
the movable stage for an object to be inspected is capable of rotational movement for main scanning, and translational movement for auxiliary scanning, and
the adjusting means increases the brightness of the illumination light beam in accordance with a degree of a linear speed of the rotational movement for the main scanning of the movable stage for an object to be inspected.

14. An optical inspection apparatus comprising a movable stage for an object to be inspected, capable of rotational movement for main scanning and translational movement for auxiliary scanning, and adapted to be substantially continuously displaced in both main scanning direction and auxiliary direction, a laser light source, an illumination optical system for irradiating a laser beam emitted from the laser light source, onto the outer surface of an object to be inspected in the form of an illumination spot having a predetermined size, a scattered/diffracted/reflected light detecting mechanism for detecting light scattered, diffracted and reflected in the illumination spot of the irradiated beam, and converting the detected light into electric signals, an A/D converter for converting the electric signals into digital data, an inspection coordinate detecting mechanism for detecting a position on the outer surface of the object to be inspected at a time corresponding to the converted digital data, as inspection coordinate data, during inspection, an object/defect determination mechanism for determining the presence of a foreign matter or a defect which is present on the outer surface of the object to be inspected or in the vicinity of the outer surface thereof, from the electric signal or the digital data, a particle size determining mechanism for calculating the size of the thus determined foreign matter or defect, from the digital data, a foreign matter/defect coordinate calculating mechanism for calculating a position coordinate value of the foreign matter or the defect on the outer surface of the object to be detected, from information delivered from the inspection coordinate detecting mechanism; wherein a foreign matter or a defect which is present on or in the vicinity of the outer surface of the object to be inspected is detected while the object to be inspected is moved and scanned at a linear speed which is different between the inner peripheral part and the outer peripheral part of the object to be inspected, and wherein the light quantity of the laser light source is controlled so as to change the intensity of the light spot between the inner peripheral part and the outer peripheral part of the object to be inspected.

15. An optical inspection apparatus as set forth in claim 14, wherein the control mechanism controls the laser light source or the light quantity adjusting mechanism in accordance with a linear speed which is determined in combination of a rotational speed (main scanning speed) and a translational speed (auxiliary scanning speed) of the movable stage for an object to be inspected.

16. An optical inspection apparatus as set forth in claim 15, wherein the control mechanism controls the laser light source or the light quantity adjusting mechanism so as to allow the intensity of the illumination spot to be proportional to about ½-th power of the linear speed over the outer surfaced of the object to be inspected in part or in its entire.

17. An optical inspection apparatus as set forth in claim 14, wherein the control mechanism controls the laser light source or the light quantity adjusting mechanism in accordance with an information of the auxiliary scanning coordinate of the movable stage for the object to be inspected.

18. An optical inspection apparatus as set forth in claim 17, further comprising a light quantity control table for previously storing information as to a relationship between the auxiliary scanning coordinates of the movable stage for an object to be inspected and as to the intensity of the illumination spot at the coordinate position, and the control mechanism controls the laser light source or the light quantity adjusting mechanism in accordance with the information of the auxiliary scanning coordinates of the movable stage for an object to be inspected, and the light quantity control table.

19. An optical type inspection apparatus as set forth in claim 18, wherein the information of the intensity of the illumination spot in the light quantity table is determined so that the temperature rise caused at the outer surface of the object to be inspected, by the irradiation of the laser beam thereonto is maintained to be substantially constant over the outer surface of the object to be inspected in part or in its entirety.

20. An optical apparatus as set forth in claim 14, wherein the foreign matter/defect determining means and the particle size calculating means correct the digital data with the intensity of the illumination spot at the time corresponding to the digital data.

21. An optical inspection apparatus as set forth in claim 20, further comprising an illumination light quantity monitor for monitoring a light quantity in proportion to the intensity of the illumination spot on an optical path from the laser light source or the light quantity adjusting means to the illumination spot, and the foreign object/defect determining means and the particle size calculating means including a correcting means for correcting the digital data with the use of a signal from the light quantity monitor.

22. An optical inspection apparatus as set forth in claim 14, wherein the intensity of the illumination spot is restrained to a lower value around the outer peripheral edge of the object to be inspected.

23. An optical inspection apparatus comprising a movable stage for an object to be inspected, capable of rotational movement for main scanning and translational movement for auxiliary scanning, and adapted to be continuously displaced in both main scanning direction and auxiliary scanning direction, a laser light source, a light quantity adjusting mechanism for adjusting a light beam emitted from the laser light source, an illumination optical system for irradiating an illumination light beam emitted from the light quantity adjusting means onto the outer surface of the object to be inspected in the form of an illumination spot having a predetermined size, a scattered/diffracted/reflected light detecting mechanism for detecting light scattered, diffracted and reflected in the illumination spot of the irradiated light beam, and converting the detected light into electric signals, an A/D converter for converting the electric signals into digital data, an inspection coordinate detecting mechanism for detecting a position on the outer surface of the object to be inspected at a time corresponding to the converted digital data, as inspection coordinate data, during inspection, a foreign matter/defect determining mechanism for determining the presence of a foreign matter or a defect which is present on or in the vicinity of the outer surface of the object to be inspected, from the electric signals or the digital data, a particle size detecting mechanism for calculating a size of the determined foreign matter or defect from the digital data, a foreign matter/defect coordinate calculating means for calculating of a position coordinate value of the foreign matter or defect on the outer surface of the object to be inspected, from information delivered from the inspection coordinate detecting mechanism; wherein a foreign matter or a defect which is present on or in the vicinity of the outer surface of the object to be inspected is detected while the object to be inspected is moved and scanned at a linear speed which is different between the inner peripheral part and the outer peripheral part of the object to be inspected, and wherein the light quantity adjusting mechanism is controlled so as to change the intensity of the illumination spot from the inner peripheral part to the outer peripheral part of the object to be inspected, or from the outer peripheral part to the inner peripheral part thereof.

24. An optical inspection apparatus as set forth in claim 23, wherein the quantity adjusting mechanism is selected from the group consisting of:
   (1) a filter having a light transmittance rate which is changed;
   (2) an optical attenuator composed of a polarizer or a polarized beam splitter, and a half-wave plate in combination; and
   (3) an acoustooptical modulator.

25. An optical inspection apparatus as set forth in claim 24, wherein the control mechanism controls the laser light source or the light quantity adjusting means so as to maintain a temperature rise caused on the outer surface of the object to be inspected by the irradiation of the laser beam, to be substantially constant over the outer surface of the object to be inspected in part or in its entirety.

* * * * *